(12) United States Patent
Na et al.

(10) Patent No.: US 9,192,360 B2
(45) Date of Patent: Nov. 24, 2015

(54) ULTRASOUND SYSTEM AND METHOD OF OBTAINING ULTRASOUND IMAGE

(71) Applicant: Samsung Medison Co., Ltd., Gangwon-do (KR)

(72) Inventors: Doo-young Na, Gangwon-do (KR); Dong-kyu Hyoung, Gangwon-do (KR)

(73) Assignee: SAMSUNG MEDISON CO., LTD., Hongcheon-Gun, Gangwon-Do (KR)

( * ) Notice: Subject to any disclaimer, the term of this patent is extended or adjusted under 35 U.S.C. 154(b) by 243 days.

(21) Appl. No.: 13/759,945

(22) Filed: Feb. 5, 2013

(65) Prior Publication Data

US 2013/0261459 A1 Oct. 3, 2013

(30) Foreign Application Priority Data

Mar. 28, 2012 (KR) ........................ 10-2012-0031817

(51) Int. Cl.
*A61B 8/14* (2006.01)
*A61B 8/00* (2006.01)
*A61B 5/0452* (2006.01)
*A61B 8/06* (2006.01)
*A61B 8/08* (2006.01)

(52) U.S. Cl.
CPC ............... *A61B 8/543* (2013.01); *A61B 5/0452* (2013.01); *A61B 8/14* (2013.01); *A61B 8/4483* (2013.01); *A61B 8/486* (2013.01); *A61B 8/488* (2013.01); *A61B 8/5207* (2013.01); *A61B 8/585* (2013.01); *A61B 8/06* (2013.01); *A61B 8/0883* (2013.01); *A61B 8/5246* (2013.01)

(58) Field of Classification Search
None
See application file for complete search history.

(56) References Cited

U.S. PATENT DOCUMENTS

| 5,513,640 | A | * | 5/1996 | Yamazaki et al. | ............ 600/455 |
| 5,709,210 | A | * | 1/1998 | Green et al. | ................. 600/453 |
| 5,735,281 | A | | 4/1998 | Rafter et al. | |

(Continued)

FOREIGN PATENT DOCUMENTS

| EP | 0 770 352 A1 | 5/1997 |
| JP | 2005-305129 A | 11/2005 |

(Continued)

OTHER PUBLICATIONS

Holfort et al. (2008). Plane wave medical ultrasound imaging using adaptive beamforming, IEEE, pp. 288-292.*

(Continued)

*Primary Examiner* — Long V Le
*Assistant Examiner* — Bradley Impink
(74) *Attorney, Agent, or Firm* — McDermott Will & Emery LLP

(57) ABSTRACT

A method of obtaining an ultrasound image, the method including: obtaining a bio cycle of an examinee comprising at least one section; setting an ultrasound mode corresponding to each of the at least one section of the bio cycle or a beam forming method; transmitting an ultrasound signal to an object of the examinee according to the set ultrasound mode or beam forming method, receiving an echo signal from the object, and obtaining ultrasound data; and generating an ultrasound image of the object by using the obtained ultrasound data.

11 Claims, 4 Drawing Sheets

(56) References Cited

U.S. PATENT DOCUMENTS

| | | | |
|---|---|---|---|
| 5,860,927 A * | 1/1999 | Sakaguchi et al. | 600/453 |
| 6,491,633 B1 | 12/2002 | Krishnan et al. | |
| 6,673,017 B1 * | 1/2004 | Jackson | 600/437 |
| 7,850,609 B2 | 12/2010 | Takimoto et al. | |
| 2002/0151795 A1 * | 10/2002 | Palti | 600/454 |
| 2007/0088213 A1 | 4/2007 | Poland | |
| 2007/0239002 A1 * | 10/2007 | Alam | 600/437 |
| 2009/0326379 A1 * | 12/2009 | Daigle et al. | 600/453 |
| 2014/0018679 A1 * | 1/2014 | Chen et al. | 600/438 |

FOREIGN PATENT DOCUMENTS

| | | |
|---|---|---|
| JP | 2007-512870 A | 5/2007 |
| JP | 2009-119250 A | 6/2009 |
| JP | 4764125 B2 | 8/2011 |

OTHER PUBLICATIONS

Jeremy Bercoff (2011). Ultrafast Ultrasound Imaging, Ultrasound Imaging—Medical Applications, Prof. Oleg Minin (Ed.), ISBN: 978-953-307-279-1, InTech, Available from: http://www.intechopen.com/books/ultrasoundimaging-medical-applications/ultrafast-ultrasound-imaging.*
Korean office action issued in Korean Application No. 10-2012-0031817 dated Mar. 19, 2014, w/English translation.
Extended European Search Report issued in European Patent Application No. 13158316.3 dated Jun. 10, 2013.
Korean Notice of Non-Final Rejection, w/ English translation thereof, issued in Korean Patent Application No. KR 10-2012-0031817 dated Aug. 30, 2013.
Korean Notice of Allowance issued in Korean Application No. 10-2012-0031817 dated Nov. 6, 2014, with English Translation.

* cited by examiner

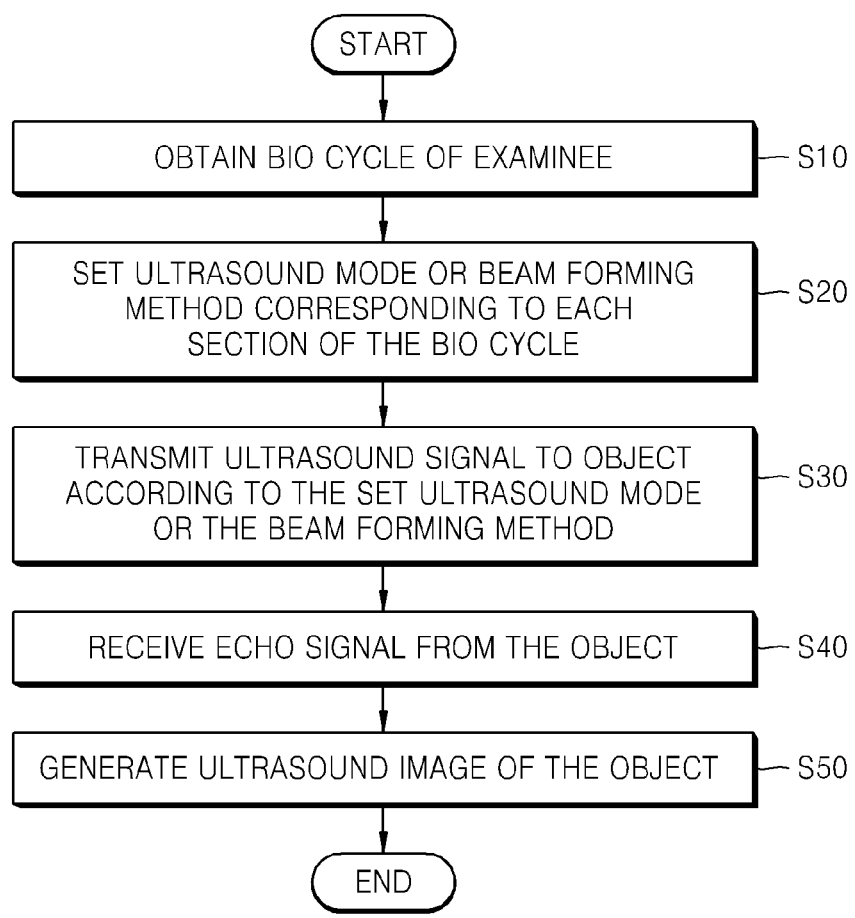

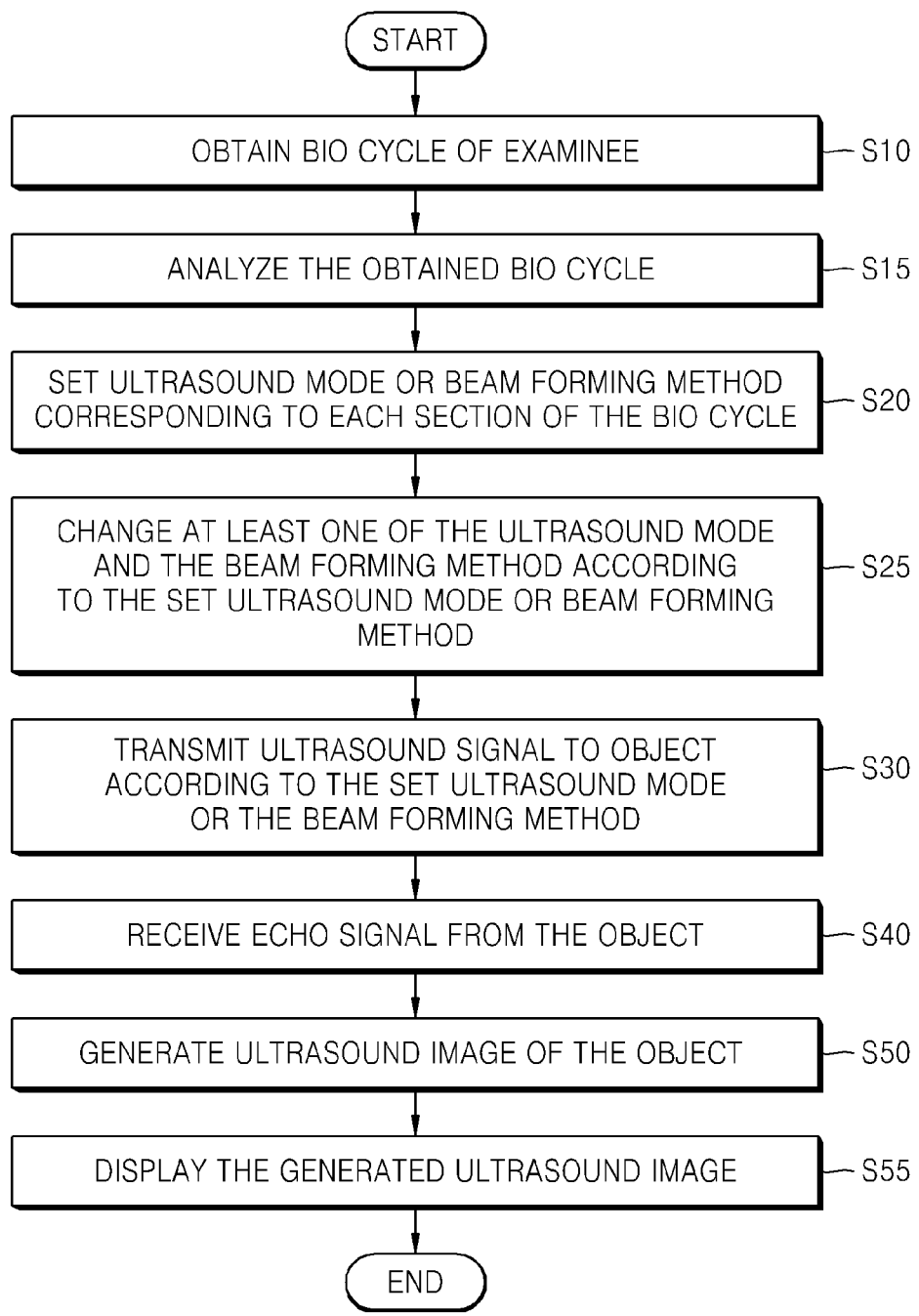

ULTRASOUND SYSTEM AND METHOD OF OBTAINING ULTRASOUND IMAGE

CROSS-REFERENCE TO RELATED PATENT APPLICATION

This application claims the benefit of Korean Patent Application No. 10-2012-0031817, filed on Mar. 28, 2012, in the Korean Intellectual Property Office, the disclosure of which is incorporated herein in its entirety by reference.

BACKGROUND OF THE INVENTION

1. Field of the Invention

The present invention relates to a method of obtaining an ultrasound image of an object and an ultrasound system, and more particularly, to a method of obtaining an ultrasound image of an object by using a bio cycle of an examinee and an ultrasound system.

2. Description of the Related Art

Ultrasound devices are equipment used to observe an inner structure of an organism. Ultrasound devices are noninvasive diagnosis devices that display structural details, internal tissues, and a fluid flow of a human body.

Ultrasound devices transmit an ultrasound signal to an object through a human body, receive an echo signal reflected from the object, and display an image of a structure inside the human body.

An ultrasound image is generally diagnosed by examining a B-image of an object, and examining a color Doppler image of an interest region of the object, a continuous wave Doppler image thereof, a pulsed Doppler image thereof, etc.

An examiner diagnoses the object by continuously changing an ultrasound mode during the examination of the B-image. However, this method causes a time delay in the examination of an ultrasound image, and fails to obtain the ultrasound image at a desired point of time in a bio cycle of an examinee since the ultrasound mode is not synchronized with the bio cycle. For example, in a case where the examiner wants to examine a continuous wave Doppler image of a heart in a QRS section of an electrocardiogram cycle having a maximum blood flow speed of the heart, the examiner needs to determine the continuous wave Doppler image of the QRS section by continuously placing a probe at a corresponding part on the B-image based on his experience. In this case, however, the continuous wave Doppler image of the QRS section may not be accurately obtained.

SUMMARY OF THE INVENTION

The present invention provides an ultrasound system and a method of obtaining an ultrasound image by using a bio cycle of an examinee, thereby automatically changing an ultrasound mode or a beam forming method corresponding to each section of the bio cycle.

The present invention also provides an ultrasound system and a method of obtaining an ultrasound image desired by an examiner by operating an ultrasound device at a minimum number of operations.

According to an aspect of the present invention, there is provided a method of obtaining an ultrasound image, the method including: obtaining a bio cycle of an examinee including at least one section; setting an ultrasound mode or a beam forming method corresponding to each of the at least one section of the bio cycle; transmitting an ultrasound signal to an object of the examinee according to the set ultrasound mode or beam forming method, receiving an echo signal from the object, and obtaining ultrasound data; and generating an ultrasound image of the object by using the obtained ultrasound data.

The method may further include: analyzing the obtained bio cycle and setting the at least one section.

The bio cycle may include at least one of an electrocardiogram cycle and a respiration cycle.

The setting may include: setting a plane wave mode or a broad beam mode in a QRS section of an electrocardiogram cycle, and set a scan line mode in other sections thereof.

The method may further include: displaying the generated ultrasound image.

According to another aspect of the present invention, there is provided an ultrasound system including: a bio cycle obtaining unit for obtaining a bio cycle of an examinee including at least one section; a control unit for setting an ultrasound mode or a beam forming method corresponding to each of the at least one section of the bio cycle; an ultrasound data obtaining unit for transmitting an ultrasound signal to an object of the examinee according to the set ultrasound mode or beam forming method, receiving an echo signal from the object, and obtaining ultrasound data; and an ultrasound image generating unit for generating an ultrasound image of the object by using the obtained ultrasound data.

The ultrasound system may further include: a bio cycle analyzing unit for analyzing the obtained bio cycle and setting the at least one section.

The bio cycle may include at least one of an electrocardiogram cycle and a respiration cycle.

The control unit may set a plane wave mode or a broad beam mode in a QRS section of an electrocardiogram cycle, and set a scan line mode in other sections thereof.

The ultrasound system may further include: a display unit for displaying the generated ultrasound image.

According to another aspect of the present invention, there is provided a computer readable recording medium having recorded thereon a program for executing the method of obtaining an ultrasound image.

BRIEF DESCRIPTION OF THE DRAWINGS

The above and other feature points and advantages of the present invention will become more apparent by describing in detail exemplary embodiments thereof with reference to the attached drawings in which:

FIG. 4 is a flowchart illustrating a method of obtaining an ultrasound image, according to an embodiment of the present invention; and FIG. 5 is a flowchart illustrating a method of obtaining an ultrasound image, according to another embodiment of the present invention.

DETAILED DESCRIPTION OF THE INVENTION

Figure 1:
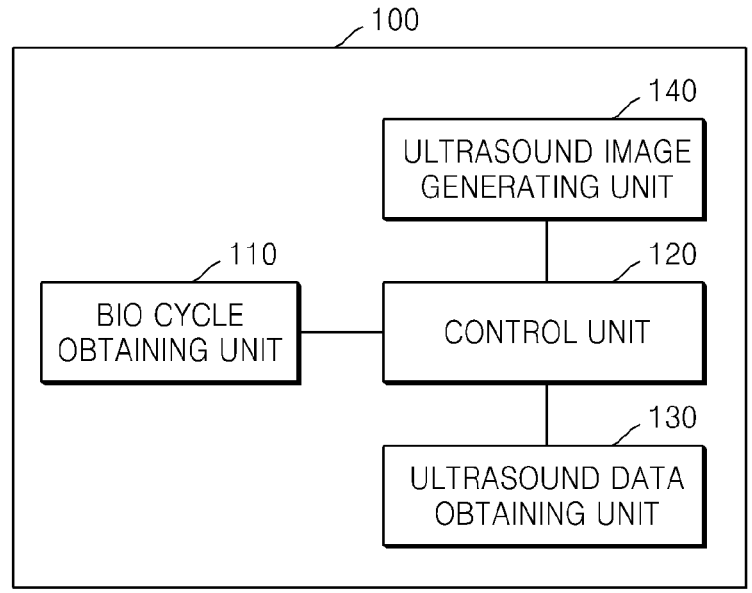
FIG. 1 is a block diagram of an ultrasound system, according to an embodiment of the present invention.

Hereinafter, the present invention will be described more fully with reference to the accompanying drawings, in which exemplary embodiments of the invention are shown. The invention may, however, be embodied in many different forms and should not be construed as being limited to the embodiments set forth herein; rather, these embodiments are provided so that this disclosure will be thorough and complete, and will fully convey the concept of the invention to those of ordinary skill in the art. Like reference numerals in the drawings denote like elements, and thus their description will be omitted.

As used herein, the term 'unit' refers to components of software or hardware such as a field-programmable gate array (FPGA) or an application specific integrated circuit (ASIC) and a 'unit' performs a particular function. However, the term 'unit' is not limited to software or hardware. A 'unit' may be configured to be included in a storage medium to be addressed or to reproduce one or more processors. Thus, examples of a 'unit' include components such as components of object-oriented software, class components, and task components, processes, functions, attributes, procedures, subroutines, segments of program codes, drives, firmware, a microcode, circuit, data, a database, data structures, tables, arrays, and parameters. Functions provided by components and 'units' may be performed by combining a smaller number of components and 'units' or further separating additional components and 'units' therefrom.

As used herein, the term "and/or" includes any and all combinations of one or more of the associated listed items. Expressions such as "at least one of," when preceding a list of elements, modify the entire list of elements and do not modify the individual elements of the list.

FIG. 1 is a block diagram of an ultrasound system 100, according to an embodiment of the present invention.

Referring to FIG. 1, the ultrasound system 100 according to an embodiment of the present invention may include a bio cycle obtaining unit 110, a control unit 120, an ultrasound data obtaining unit 130, or an ultrasound image generating unit 140. The bio cycle obtaining unit 110, the control unit 120, or the ultrasound image generating unit 140 may be implemented as micro chips.

The bio cycle obtaining unit 110 obtains a bio cycle of an examinee. The bio cycle may include an electrocardiogram cycle, a respiration cycle, etc. The bio cycle may include at least one section. For example, the electrocardiogram cycle includes a PQ section, a QRS section, and an ST section. The bio cycle obtaining unit 110 may obtain the electrocardiogram cycle by examining electrocardiogram of a heart, and may obtain the bio cycle by using various well-known methods.

The control unit 120 sets an ultrasound mode or a beam forming method corresponding to each section of the obtained bio cycle. Such a setting of the control unit 120 may be made by a user.

The ultrasound mode may include one of an amplitude (A) mode, a brightness (B) mode, a color flow image (C) mode, a Doppler (D) mode, and a motion (M) mode, and may include ultrasound modes that are obvious to one of ordinary skill in the art.

The beam forming method is a method of adjusting a form of an ultrasound beam transmitted to an object and a region of the object that reflects an echo signal.

The beam forming method may include one of a scan line mode, a broad beam mode, a plane wave mode, TX focusing, RX focusing, and dynamic receiving focusing, and may include beam forming methods that are obvious to one of ordinary skill in the art.

The scan line mode is a method of forming an ultrasound image by transmitting and receiving a focused ultrasound signal by using a predetermined number of element groups among a plurality of elements of the ultrasound data obtaining unit 130 and then transmitting and receiving the focused ultrasound signal by using the elements groups that move by a predetermined unit according to scan lines.

The broad beam mode is a method of forming an ultrasound image by transmitting and receiving a first out-of-focus ultrasound signal by using a predetermined number of element groups among a plurality of elements of the ultrasound data obtaining unit 130 and then transmitting and receiving a second out-of-focus ultrasound signal which overlaps with the first out-of-focus ultrasound signal by using the elements groups that move by a predetermined unit.

The plane wave mode is a method of forming an ultrasound image by transmitting and receiving an out-of-focus ultrasound signal by using all elements of the ultrasound data obtaining unit 130.

The scan line mode has a high image resolution and a low temporal resolution, whereas the plane wave mode has a low image resolution and a high temporal resolution. Thus, the plane wave mode may be used in a section in which a movement of an object is mainly observed.

The TX focusing is a method of collecting transmitted ultrasound waves at a point by using a focusing delay.

The RX focusing is a method of correcting a time difference that occurs in a pulse of an ultrasound echo signal reflected from an object according to a distance difference. The RX focusing may be performed by applying a time delay set according to a depth of the object.

The dynamic receiving focusing means having several receiving focuses. For example, it three points of 3 cm, 6 cm, and 9 cm are set as receiving focuses, a time delay set according to a depth at each of the three receiving focuses is dynamically applied. The dynamic receiving focusing may perform a receiving focusing continuously without restriction to the number of receiving focuses.

The ultrasound data obtaining unit 130 includes a transducer including the plurality of elements that are piezoelectric devices. The transducer transmits or receives an ultrasound signal through the plurality of elements. The ultrasound data obtaining unit 130 transmits the ultrasound signal to the object of the examinee according to the ultrasound mode set by the control unit 120 and receives the echo signal reflected from the object. In the present specification, the term "object" means various organs inside a body or a specific part inside the body from which the ultrasound image is to be obtained.

The ultrasound image generating unit 140 generates the ultrasound image of the object by using ultrasound data obtained by the ultrasound data obtaining unit 130.

Figure 2:
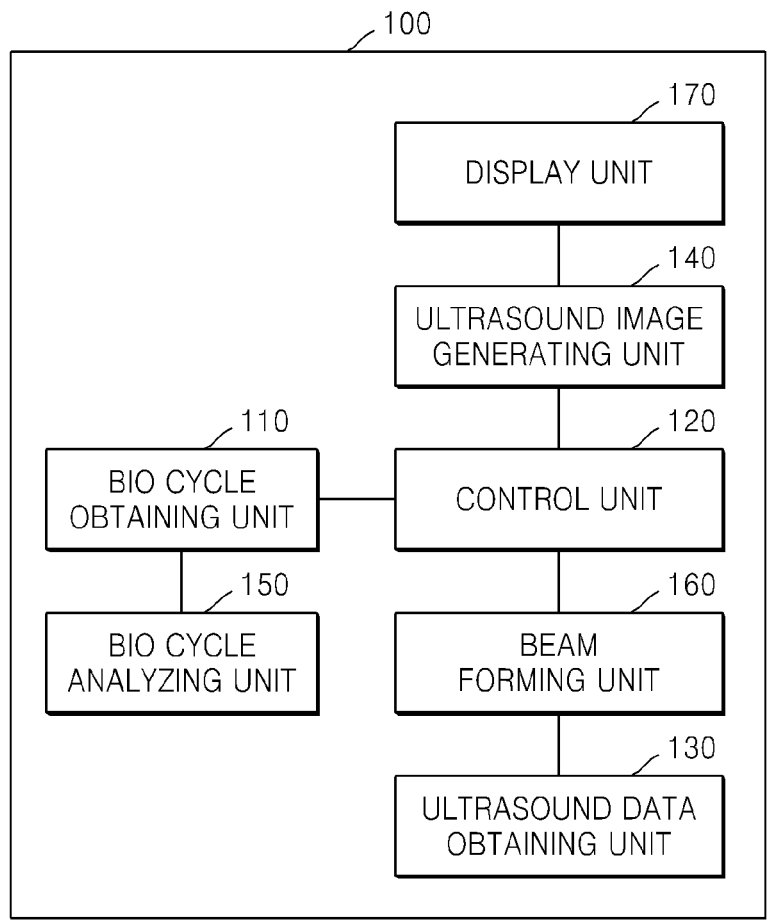
FIG. 2 is a block diagram of an ultrasound system, according to another embodiment of the present invention.

FIG. 2 is a block diagram of the ultrasound system 100, according to an embodiment of the present invention.

Referring to FIG. 2, the ultrasound system 100 according to another embodiment of the present invention may include a bio cycle analyzing unit 150, a beam forming unit 160, or a display unit 170, in addition to the bio cycle obtaining unit 110, the control unit 120, the ultrasound data obtaining unit 130, and the ultrasound image generating unit 140.

The bio cycle analyzing unit 150 analyzes a bio cycle obtained by the bio cycle obtaining unit 110 and sets at least one section of the bio cycle.

The beam forming unit 160 changes at least one of an ultrasound mode and a beam forming method according to an ultrasound mode or a beam forming method set by the control unit 120. That is, the beam forming unit 160 changes at least one of the ultrasound mode and the beam forming method according to the ultrasound mode or the beam forming method corresponding to each section of the bio cycle so that an ultrasound signal according to the changed mode may be transmitted and received through the ultrasound data obtaining unit 130.

The beam forming unit 160 may include a transmitting beam forming unit (not shown) and a receiving beam forming unit (not shown).

The transmitting beam forming unit includes a plurality of signal generating units each generating a focused ultrasound signal by using a signal delay and/or a phase change.

The receiving beam forming unit focuses a plurality of echo signals received by the ultrasound data obtaining unit 130 and converts the plurality of echo signals into a single signal. Distances between a plurality of elements included in the ultrasound data obtaining unit 130 and an object that is a focusing target are different, and thus the echo signals reflected from the object are not received by the ultrasound data obtaining unit 130 at the same point of time. Therefore, the receiving beam forming unit converts the plurality of echo signals into a single signal by applying a temporal delay to the received echo signals.

More specifically, the beam forming unit 160 adjusts the transmitting beam forming unit and the receiving beam forming unit to change at least one of the ultrasound mode and the beam forming method set by the control unit 120.

The display unit 170 displays the ultrasound image generated by the ultrasound image generating unit 140 to a user. The display unit 170 may include a monitor.

Figure 3:
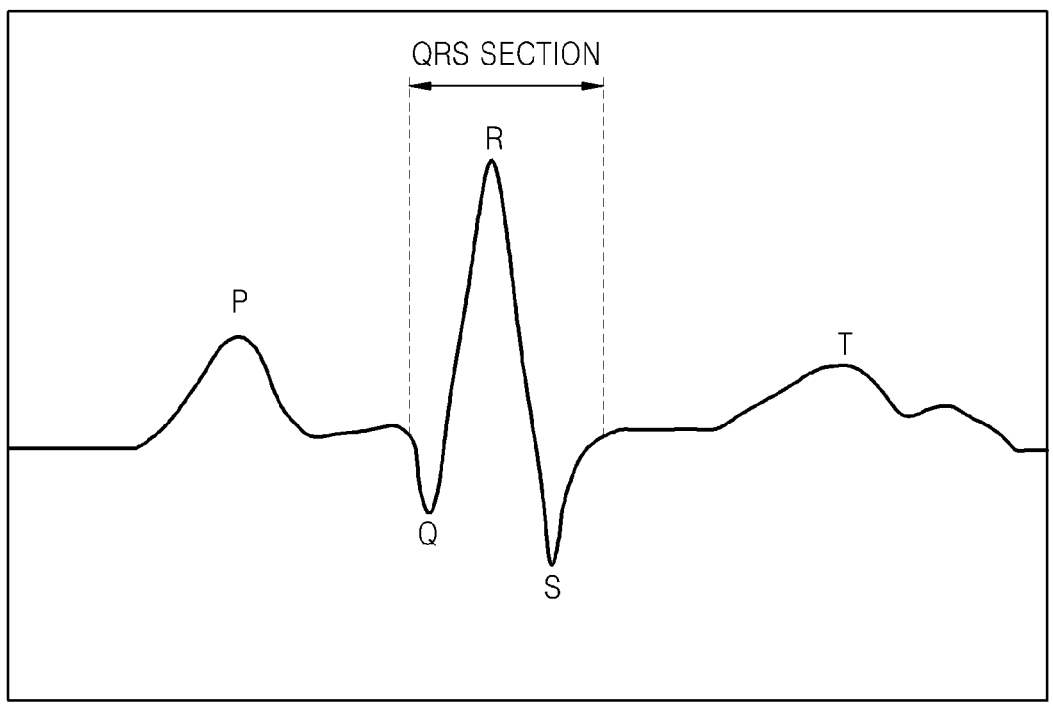
FIG. 3 is a graph of an electrocardiogram.

FIG. 3 is a graph of an electrocardiogram.

Referring to FIG. 3, a PQ section is an atrium depolarization section, a QRS section is a ventricle depolarization section, and an ST section is an atrium re-depolarization section. In the QRS section, a ventricle depolarization occurs and thus a ventricle contraction occurs. The QRS section has a maximum blood flow of a heart, and thus it may be important to observe a movement of a blood flow. Therefore, the control unit 120 of the ultrasound system 100 according to an embodiment of the present invention may set a plane wave mode having a high temporal resolution in the QRS section and set a scan line mode in the PQ section and the ST section.

FIG. 4 is a flowchart illustrating a method of obtaining an ultrasound image, according to an embodiment of the present invention. Referring to FIG. 4, the method according to an embodiment of the present invention includes operations that are sequentially performed by the ultrasound system 100 of FIGS. 1 and 2. Thus, although omitted below, the detailed description of the ultrasound system 100 of FIGS. 1 and 2 may be applied to the method of FIG. 4.

In operation S10, the bio cycle obtaining unit 110 obtains a bio cycle of an examinee. The bio cycle may include an electrocardiogram cycle, a respiration cycle, etc.

In operation S20, the control unit 120 sets an ultrasound mode or a beam forming method corresponding to each section of the bio cycle. For example, the control unit 120 may set a plane wave mode in a QRS section of the electrocardiogram cycle, and set a scan line mode in other sections thereof.

In operation S30, the ultrasound data obtaining unit 130 transmits an ultrasound signal to an object according to the ultrasound mode or a beam forming method set by the control unit 120.

In operation S40, the ultrasound data obtaining unit 130 receives an echo signal from the object.

In operation S50, the ultrasound image generating unit 140 generates an ultrasound image of the object by using the received echo signal.

FIG. 5 is a flowchart illustrating a method of obtaining an ultrasound image, according to another embodiment of the present invention.

In operation S10, the bio cycle obtaining unit 110 obtains a bio cycle of an examinee.

In operation S15, the bio cycle analyzing unit 150 analyzes the obtained bio cycle and sets at least one section of the bio cycle.

In operation S20, the control unit 120 sets an ultrasound mode or a beam forming method corresponding to each section of the bio cycle. For example, the control unit 120 may set a plane wave mode in a QRS section of an electrocardiogram cycle, and set a scan line mode in other sections thereof.

In operation S25, the beam forming unit 160 changes at least one of the ultrasound mode and the beam forming method according to the set ultrasound mode or beam forming method.

In operation S30, the ultrasound data obtaining unit 130 transmits an ultrasound signal to an object according to the ultrasound mode or the beam forming method set by the control unit 120.

In operation S40, the ultrasound data obtaining unit 130 receives an echo signal from the object.

In operation S50, the ultrasound image generating unit 140 generates an ultrasound image of the object by using the received echo signal.

In operation S55, the display unit 170 displays the generated ultrasound image.

The embodiments of the present invention can be written as computer programs and can be implemented in general-use digital computers that execute the programs using a computer readable recording medium. Examples of the computer readable recording medium include magnetic storage media (e.g., ROM, floppy disks, hard disks, etc.), and storage media such as optical recording media (e.g., CD-ROMs, or DVDs).

An ultrasound system and a method of obtaining an ultrasound image according to the above embodiments of the present invention automatically changes an ultrasound mode corresponding to each section of a bio cycle of an examinee by using the bio cycle.

The ultrasound system and the method of obtaining an ultrasound image according to the above embodiments of the present invention may also obtain an ultrasound image desired by the examinee at an accurate point of time in the bio cycle of the examinee.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A method of obtaining an ultrasound image, the method comprising:
    obtaining a bio cycle of an examinee comprising a plurality of sections including a first section and a second section;
    setting a first beam forming method corresponding to the first section in the bio cycle and a second beam forming method corresponding to the second section in the bio cycle, wherein the first beam forming method has a higher temporal resolution than the second beam forming method;
    transmitting an ultrasound signal to an object of the examinee according to the set first and second beam forming methods, receiving an echo signal from the object, and obtaining ultrasound data; and
    generating an ultrasound image of the object by using the obtained ultrasound data;
    wherein the bio cycle is an electrocardiogram cycle, and the first beam forming method includes a plane wave mode or a broad beam mode in a QRS section of the electrocardiogram cycle, and the second beam forming method includes a scan line mode in other sections of the electrocardiogram cycle.

2. The method of claim 1, further comprising: analyzing the obtained bio cycle and setting the plurality of sections.

3. The method of claim 1, wherein the bio cycle further comprises a respiration cycle.

4. The method of claim 1, further comprising: displaying the generated ultrasound image.

5. A non-transitory computer readable recording medium having recorded thereon a program for executing the method of claim 1.

6. The method of claim 1, wherein a maximum blood flow velocity occurs during the QRS section of the electrocardiogram cycle.

7. An ultrasound system comprising:
a processor configured to obtain a bio cycle of an examinee comprising a plurality of sections including a first section and a second section, and to set a first beam forming method corresponding to the first section in the bio cycle and a second beam forming method corresponding to the second section in the bio cycle, wherein the first beam forming method has a higher temporal resolution than the second beam forming method; and
an ultrasound transducer configured to transmit an ultrasound signal to an object of the examinee according to the set first and second beam forming methods, receive an echo signal from the object, and obtain ultrasound data, wherein the processor is further configured to generate an ultrasound image of the object by using the obtained ultrasound data;
wherein the bio cycle is an electrocardiogram cycle, and the first beam forming method includes a plane wave mode or a broad beam mode in a QRS section of the electrocardiogram cycle, and the second beam forming method includes a scan line mode in other sections of the electrocardiogram cycle.

8. The ultrasound system of claim 7, wherein the processor is further configured to analyze the obtained bio cycle and set the plurality of sections.

9. The ultrasound system of claim 7, wherein the bio cycle further comprises a respiration cycle.

10. The ultrasound system of claim 7, further comprising: a display for displaying the generated ultrasound image.

11. The method of claim 7, wherein a maximum blood flow velocity occurs during the QRS section of the electrocardiogram cycle.

* * * * *